United States Patent [19]

Bumpus et al.

[11] Patent Number: 4,931,055
[45] Date of Patent: Jun. 5, 1990

[54] DISTRACTION RODS

[76] Inventors: John Bumpus, 73 Trobriand Crescent, Glenfield, NSW 2167; Trevor Woodbridge, 31 Harp Street, South Belmore, NSW 2192, both of Australia

[21] Appl. No.: 174,998
[22] PCT Filed: Jun. 1, 1987
[86] PCT No.: PCT/AU87/00160
§ 371 Date: Jan. 26, 1988
§ 102(e) Date: Jan. 26, 1988
[87] PCT Pub. No.: WO87/07134
PCT Pub. Date: Dec. 3, 1987

[51] Int. Cl.$^5$ ................................. A61F 5/04
[52] U.S. Cl. ............................. 606/60; 606/61
[58] Field of Search ............ 128/69, 92 R, 92 YL, 128/92 YM; 623/17

[56] References Cited
U.S. PATENT DOCUMENTS 4,404,967  9/1983  Bacal et al. .................... 128/69
4,658,809  4/1987  Ulrich et al. ................ 128/92 YM

FOREIGN PATENT DOCUMENTS 0188954   7/1986   European Pat. Off. ............ 623/17
0735248   6/1980   U.S.S.R. .................... 128/69
1022702   6/1983   U.S.S.R. .................... 128/69
1127578  12/1984   U.S.S.R. .................. 128/92 YM Primary Examiner—Mickey Yu
Assistant Examiner—Charles H. Sam
Attorney, Agent, or Firm—Limbach, Limbach & Sutton

[57] ABSTRACT

Distraction rods for use in the treatment of curvature of the spine and comprising an elongated member having a threaded, axial bore therein and an elongated housing into which the elongated member is slidably fitted, the elongated housing having located at one end a connection means for fitting to a clamp for connection to the vertebra, and wherein at the other end of the elongated housing a second connection means for fitting to another clamp for connection to the vertebra is located on one end of the elongated member, said elongated housing having a threaded rod which fits within the bore of the elongated member and engages the threaded bore therein such that the elongated member can move longitudinally along the threaded rod, and hence longitudinally with respect to the elongated housing.

5 Claims, 4 Drawing Sheets

DISTRACTION RODS

The present invention relates to spinal rods, and in particularly, to an improved system of spinal rodding of subcutaneous, compression and distraction rods which are used in the treatment of patients suffering from anomalies in the curvatuve of the spine. The systems are inserted internally and are hooked onto the respective vertebrae to support the spine, to prevent such from growing incorrectly during child growth and initially give correction to both children and adolescents.

The prior art such as those shown in FIG. 1 comprise both spinal rods 16 and 17 which comprise a threaded rod 17 with a hook like connector 19 located at one end with a similar hook like connector 18 having an internal thread to engage on the threaded rod 17 to move up and down the threaded rod 17; the position of the second hook like connector being stabilised by a nut located on the threaded shaft. For insertion into the patient, a major operation is required to allow access to the spine for a length some distance greater than the total length of the rod. As the rods are also inserted in children, it is necessary, due to the growth of the child, that the hook like connections are adjusted to ensure correct contact with the respective vertebra, as the child grows. To allow for this adjustment, a section of the threaded rod must extend past the top hook like connector. However, to prevent this shaft from protruding through the patient's skin, it is necessary that only a small length of rod extend beyond the adjustable hook like connector.

The present invention will now be described with reference to the accompanying drawings in which.

Figure 1:
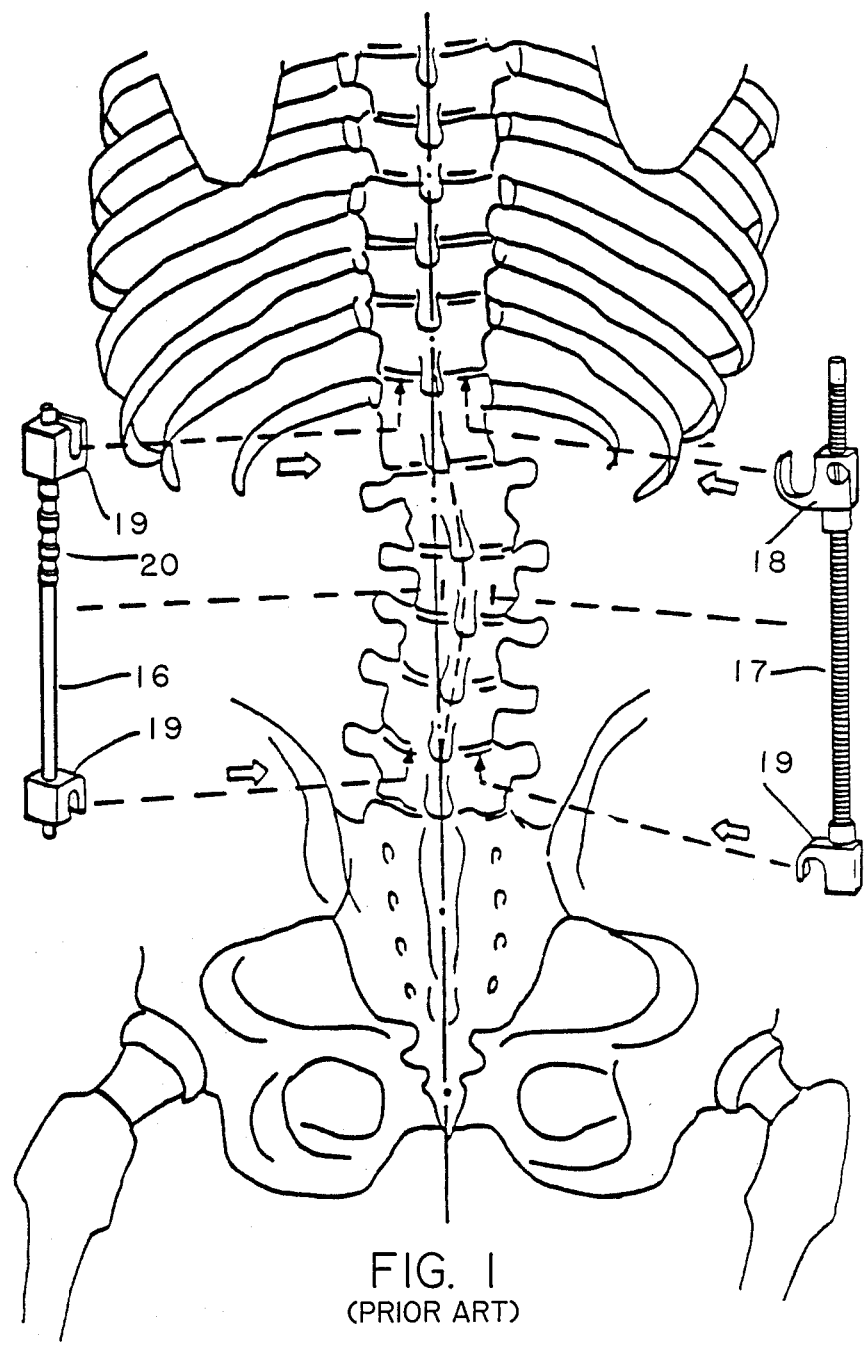
FIG. 1 is a schematic representation of the prior art showing how it is used.
Figure 2:
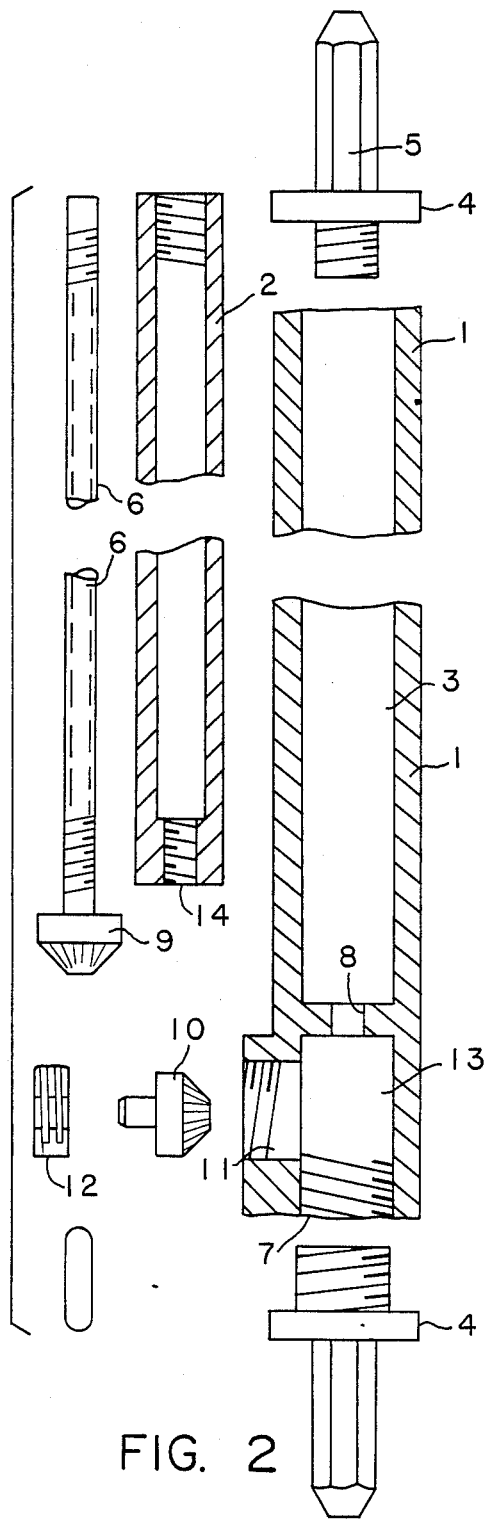
FIG. 2 shows an exploded view of one embodiment of the present invention.
Figure 3:
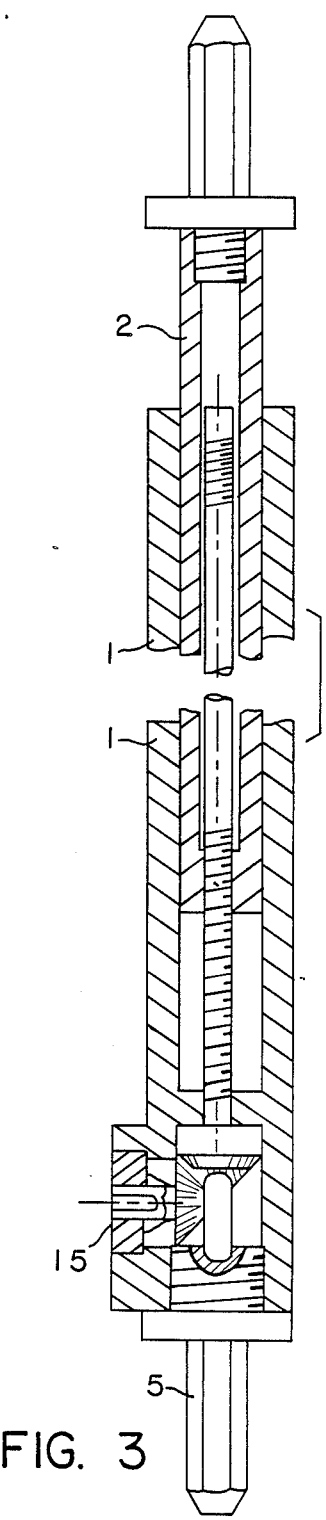
FIG. 3 shows a cutaway assembly view of the embodiment shown in FIG. 2.

A distraction rod made in accordance with one embodiment of the present invention is as shown in the FIGS. 2 and 3 and comprises an elongated housing 1 into which an elongated member 2 slidably fits. The fit between the housing 1 and the member 2 is such to prevent the ingress of tissue and body fluids into the cavity 3 of the housing. Located at the top of the elongated member 2 is a connection 4, for the hook like vertebra connectors (not shown). The connectors 4 have a non circular connecting rod 5 to prevent the hook like connectors from rotating thereon. The profile of the connecting rods 5 can be any shape, such as rectangular, square, hexagonal, octagonal or elliptical.

A drive rod 6 is inserted through the lower end 7 of the housing 1 to extend through the neck 8 into the cavity 3. The drive rod 6 has located at its lower end a bevel gear 9. The drive gear 10 is inserted through the opening 11 to engage the bevel gear 9 of the drive rod 6. A locking means 12 is inserted into the opening 11 to hold the drive gear 10 in position and to co-operate with the drive gear 10 to prevent the ingress of any tissue or body fluids into the gear housing 13.

The drive rod 6 is threaded and mates with a complimentary threaded section 14 of the elongated member 2 (as shown in FIG. 3). Connection 4 is inserted into the lower end 7 to seal said gear housing 13.

In use it is necessary that the patient's spine be exposed and that the vertebra hook like clamps (not shown) are connected to the respective connectors 4, and the drive gear operated to extend the elongated member 2 to position the vertebra clamps at the appropriate position, and the drive gear 10 is operated to correctly increase the length of the distraction rod to the appropriate position needed for the patient. The drive gear 10 can be operated by any suitable connection, such as an Allen wrench socket 15, as shown in FIG. 3. This socket would be positioned facing toward the patient's skin.

Figure 4:
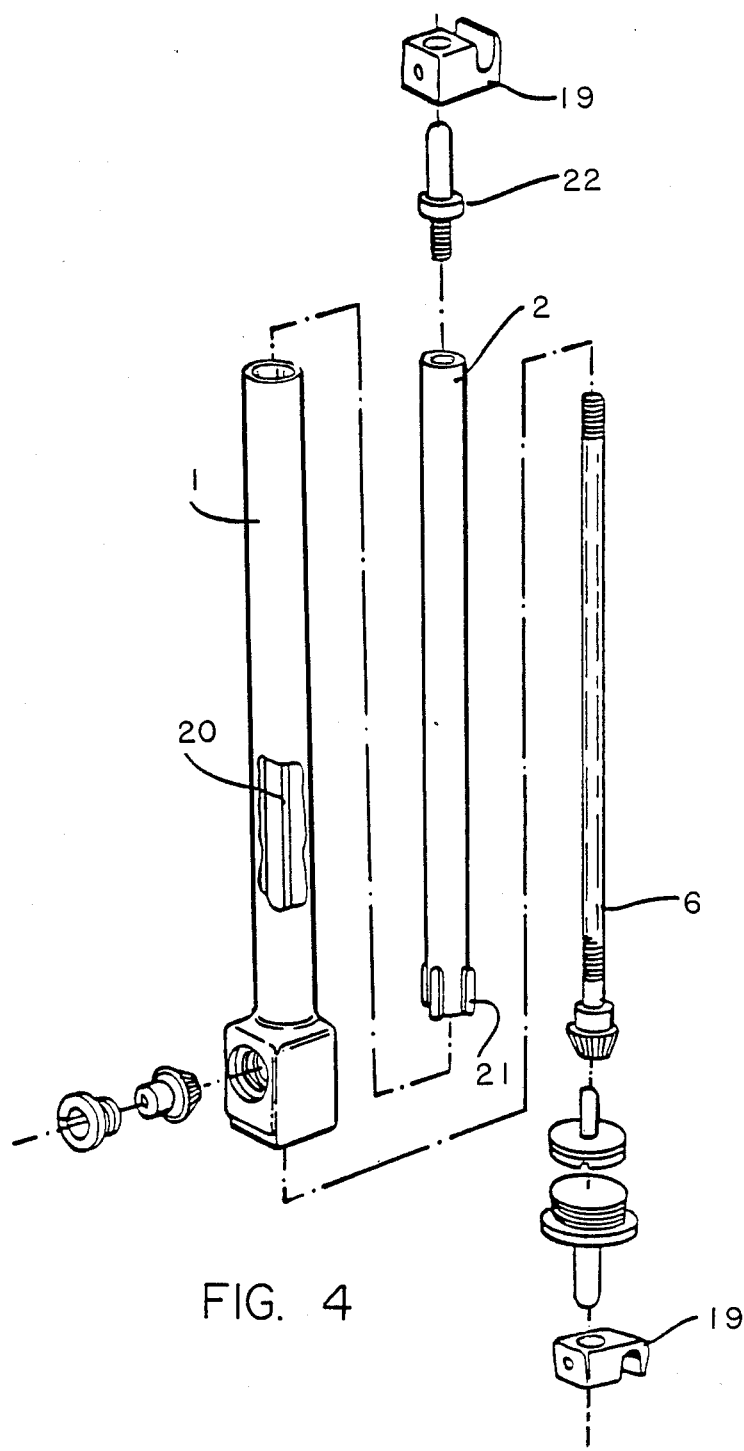
FIG. 4 illustrates another embodiment of the present invention.

A further embodiment is shown in FIG. 4. This distraction rod is similar in construction to the previous embodiment providing further advantages over the prior art.

However, the housing 1 has lands or grooves 20 running the length of the housing 1, and the elongated member 2 has projections 21 which abut against the lands 20 or, fit within the grooves 20, to prevent rotation of the elongated member 2 with respect to the housing 1.

The elongated member 2 has an internal threaded section (not shown) which engages the threads of the drive rod 6 similar to the previous embodiment.

Because of the non rotation of the elongated member 2 the hook connector 22, has a circular profile connector rod, suitable to receive standard spinal hooks.

Figure 5:
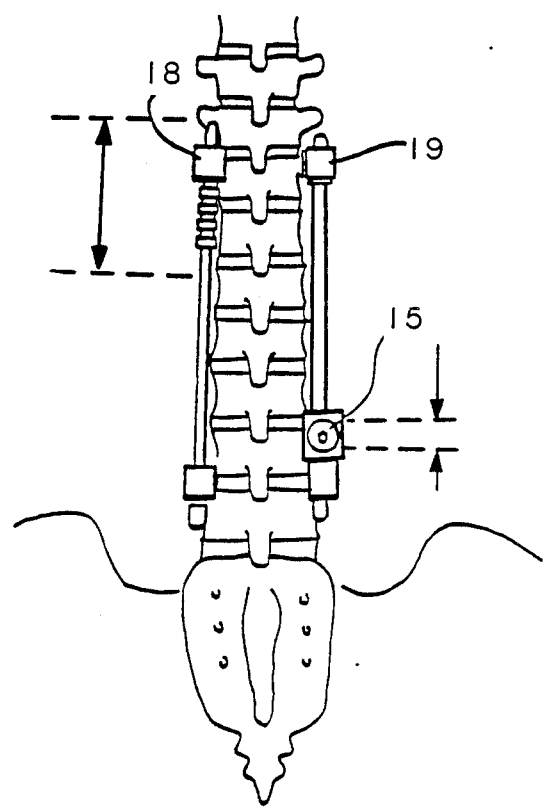
FIG. 5 is a schematic representation of a prior art rod and a distraction rod according to one embodiment of the present invention, shown in use, not necessarily showing correct surgical placement into the spine.

The operation required to insert the spinal rods of the present invention would be similar in nature to that of the prior art rods. However, to increase the length of the spinal rod of the present invention, as shown in the FIG. 5, a minor operation is required to expose the Allen wrench socket 15 as compared to the larger operation required in the prior art. An Allen wrench is fitted into the said socket to turn the drive bevel gear 10 which, in turn, rotates the drive rod 6 which interacts with the threaded section 14 of the elongated member 2 which, because the vertebra clamp is fixed with respect to the spine and is rotatably fixed to the connections 4, cause the elongated member 2 to be extended along the threads of the drive rod 6, extending the distance between the two vertebra clamps. There is no necessity to operate near the connection of the vertebra clamps to the spine, as is the case with the prior art rods, as the only operation required is that to gain access to the Allen wrench socket, with regard to the "increasing section" of the future adjustment operations.

In order to allow the rod to be bent to fit the body contour at the top end, the manufacture would be as in FIG. 4 but having the housing 1 20 mm shorter than that shown in FIG. 4 to allow for bending of the elongated member 2 without disturbing the mechanism; this being the preferred bending means.

The rod does not extend to any appreciable distance beyond the vertebra clamps and, as the elongated member 2 is telescopically located with the housing 1, the rod can continue to be used throughout the growth of the greater majority of children suffering from spinal disorders. Thus, rather than the children suffering major surgery many times in their life when a prior art rod is used, the children would only require one major operation to implant the distraction rod of the present invention, and minor operations to expose the drive connection to lengthen the rod. Therefore, the patients would be exposed to less trauma with the implantation of the present invention than with the existing devices.

In the prior art, to perform compression it is necessary to use a full threaded rod along which the hook like connectors are threaded in reverse positions. The position of the hook like connectors is adjusted by means of respective nuts screwed along the threaded rod. The hook like connectors are positioned and the nuts tightened forcing the hook like connector towards each other to provide compression on the vertebra.

In embodiments of the present invention, the distraction rod has to be modified to be used for compression. The top and bottom connectors 4 are removed and replaced with threaded sections of the required length. The hook like connectors are turned to face each other and are screwed along the respective threaded section to the appropriate locations and are held in place with nuts, or are simply slipped over the threaded section and are held in place by nuts. To apply compression the elongated member is withdrawn into the housing by means of the drive means forcing the hook like projections to move towards each other.

In a further form of the invention there is provided a distraction rod which comprises:

an elongated member having at one end a connection means adapted to connect a vertebra clamp non rotatably thereto and provided at the other end with a threaded section;

a housing adapted to engage over said threaded section to interact and rotate along said threaded section, said housing being adapted to support a vertebra clamp rotatably thereon; and a drive means adapted to engage with said housing such that, when said drive means is operated, said housing rotates and climbs along said threaded section, moving said vertebra clamp associated therewith.

Preferably the drive means is carried by said vertebra clamp, and the elongated member is of a diameter such that it can be bent to conform with the curvature of the patient's spine.

The drive means can comprise any suitable connection, but preferably would be similar construction as to that described with the previous embodiment, utilising bevel gears or the like.

As the present invention is made from materials such as 316L medical grade stainless steel or titanium alloys which are inert to action from the tissue and body fluids, and the construction is such to prevent the ingress of tissue and body fluids between the moving surfaces, the present invention provides an improved spinal rod which possesses many advantages over those of the prior arts.

Embodiment of the present invention provide the following advantages over the prior art:
1. No projection of the rod beyond the hook and as such the rod will not pierce the skin.
2. Reduction in rod exchanges, due to increased useable life of the rod.
3. No thread or ratchet cleansing/dissecting of biological growth.
4. Smaller adjustment operation.
5. Less scarring.
6. May show greater control as can be adjusted more often.
7. Due to ease, increased usage to wider number of patients.
8. Smaller removal operation, no thread or ratchet cleaning. 9. Less patient trauma, hospitalisation, recuperation.
10. Finer increase of any given amount, rather than 0.27", in ratchet system, giving to better control of correction, both initially and subsequent.
11. Due to fine increase, less neurological related problems.
12. Increase above lower hook at a central point, giving to less opening of wound by a large degree.
13. No need of re-opening of subcutaneous tissue on rod increases.
14. Can be bent and still increased, such not available in any prior system.
15. Easier to place into purchase sites.
16. Locks interiorally, alleviating need for 'C' clips or thread destroying.
17. Covers all fields in which both ratchet and threaded rods are used all parts may be exchanged for different applications.

It should be obvious that modifications could be made to the above description, such as the method of driving the drive gear and the type of engagement between the gears, without departing from the spirit and the scope of the present invention.
18. Can take child or adult hooks by exchanging the supports.
19. Less likelyhood of snapping and hence reducing the likelyhood of litigation.
20. Less bending opportunity, after placement.
21. No sharp edges.
22. Inner shaft may be made to fit numerous hooks and still maintain its non pulling of flesh on increase.
23. For compression, hooks can be firstly placed and nuts introduced to maintain position, now rod may be decreased to effect desired compression, rather than continual nut movement.
24. For fractures again as above, rod may utilise compression, from a central point.
25. Better ease of distraction during fusions, or compression.
26. To remove, can screw out of hooks, rather than snap rod, and again no need to clean ratchet/thread, of tissue growth.
27. The rod has significant advantages over the ratchet and threaded systems, due to easier placement, easier removal, greater control, finer correction and patient alleviation of trauma. Such also being an advantage in patient not desiring rod increase.

Following is a list of attachments for embodiments of the present invention:
1. Seals (optional)—Silastic or other suitable plastics material. All attachments have hexagonal removal section.

TOP

2. Hook support round.
3. Hook support 20 mm longer round. (For bending.)
4. Hook support round with thread section protruding some ⅛".
5. Thread Section (any length) for compression.
6. Multi hook design.

BOTTOM

7. Round hook support.
8. Round 20 mm longer hook support (bending)
9. Round hook support with thread of some ⅛"—(Fractures).

10. Square hook support.
11. Square 20 mm longer hook support.
12. Square hook support with thread of some ⅛".
13. Screw in thread compression section (any length).

TOOLS

14. Double end spanner.
15. Surgical driver.
16. Bending tool.

We claim:

1. A distraction rod comprising an elongated member having a threaded, axial bore therein and an elongated housing into which the elongated member is slidably fitted, the elongated housing having located at one end a connection means for fitting to a clamp for connection to the vertebra, and wherein at the other end of the elongated housing a second connection means for fitting to another clamp for connection to the vertebra is located on one end of the elongated member, said elongated housing having operating means which comprises a threaded rod which fits within the bore of the elongated member and engages the threaded bore therein such that the elongated member can move longitudinally along the threaded rod, and hence longitudinally with respect to said elongated housing.

2. A distraction rod according to claim 1 wherein the elongated housing is closed at one end and open at the other end and wherein the threaded rod has one end which engages the threads of the axial bore within the elongated member and another end which bears against the closed end of the elongated housing and wherein the operating means further comprises means for rotating the threaded rod relative to the elongated member.

3. A distraction rod according to claim 1 wherein said operating means comprises a right angle drive.

4. A distraction rod according to claim 3 wherein said right angle drive comprises a bevel gear operable externally of the housing which meshes with a bevel gear on one end of the threaded rod.

5. A distraction rod according to claim 4 wherein said right angle drive is operated by an allen wrench.

* * * * *